(12) United States Patent
Otani et al.

(10) Patent No.: US 8,536,548 B2
(45) Date of Patent: Sep. 17, 2013

(54) PARTICLE BEAM THERAPY SYSTEM

(75) Inventors: Toshihiro Otani, Chiyoda-ku (JP);
Takeshi Hagino, Chiyoda-ku (JP);
Koichi Ikuta, Chiyoda-ku (JP)

(73) Assignee: Mitsubishi Electric Corporation, Chiyoda-Ku, Tokyo (JP)

( * ) Notice: Subject to any disclaimer, the term of this patent is extended or adjusted under 35 U.S.C. 154(b) by 98 days.

(21) Appl. No.: 13/260,865

(22) PCT Filed: Feb. 23, 2011

(86) PCT No.: PCT/JP2011/053924
§ 371 (c)(1),
(2), (4) Date: Sep. 28, 2011

(87) PCT Pub. No.: WO2012/114465
PCT Pub. Date: Aug. 30, 2012

(65) Prior Publication Data
US 2012/0215049 A1    Aug. 23, 2012

(51) Int. Cl.
*G21K 5/04*    (2006.01)

(52) U.S. Cl.
USPC .......... 250/492.3; 250/492.1; 250/505.1; 250/515.1; 378/145; 378/147; 378/148; 378/149; 378/150; 378/152; 600/1

(58) Field of Classification Search
USPC .......... 378/145, 147, 148, 149, 150, 152, 378/153; 250/491.1, 492.1, 492.3, 505.1, 250/515.1; 600/1, 2
See application file for complete search history.

(56) References Cited

U.S. PATENT DOCUMENTS 5,684,854 A    11/1997   Hughes
2007/0176126 A1*   8/2007   Hashimoto ............... 250/495.1
2008/0298553 A1*   12/2008   Takahashi et al. ............ 378/152
2011/0204262 A1    8/2011   Pu et al.
2012/0205530 A1*   8/2012   Beaulieu et al. .......... 250/252.1

FOREIGN PATENT DOCUMENTS

| JP | 10-076019 A | 3/1998 |
| JP | 2008-295860 A | 12/2008 |
| JP | 2010-104452 A | 5/2010 |
| WO | WO 2010/073318 A1 | 7/2010 |

OTHER PUBLICATIONS

International Search Report (PCT/ISA/210) issued on Mar. 22, 2011, by Japanese Patent Office as the International Searching Authority for International Application No. PCT/JP2011/053924.
Written Opinion (PCT/ISA/237) issued on Mar. 22, 2011, by Japanese Patent Office as the International Searching Authority for International Application No. PCT/JP2011/053924.

* cited by examiner

Primary Examiner — Nicole Ippolito
(74) Attorney, Agent, or Firm — Buchanan Ingersoll & Rooney PC

(57) ABSTRACT

A particle beam therapy system that prevents dispersion of a charged particle beam, reduction of the energy thereof, and upsizing of the system and can accurately monitor the opening shape of a multileaf collimator so as to perform high-accuracy particle beam therapy. An image-capturing unit that takes an image of an outer end of a respective downstream side face of a leaf plate is provided for each row of leaves in such a way as to be situated at a position that is at an outer side of an irradiation field; and adjusted in such a way that a foot of a perpendicular line from a viewpoint, of the image capturing unit, to the downstream side face of a leaf plate, is situated at a position that is at an inner side of the position of the outer end when the leaf plate is maximally driven in the departing direction.

16 Claims, 7 Drawing Sheets

US 8,536,548 B2

PARTICLE BEAM THERAPY SYSTEM

TECHNICAL FIELD

The present invention relates to a particle beam therapy system that performs therapy by irradiating a particle beam onto a diseased site of a patient, and particularly to a particle beam therapy system that can perform irradiation with an irradiation shape conforming to a diseased site, by use of a multileaf collimator.

BACKGROUND ART

Some particle beam therapy systems shape an irradiation field through a multileaf collimator so as to irradiate a particle beam in an irradiation shape based on a treatment plan. In such a particle beam therapy system, in the case where during irradiation of a particle beam, the opening shape of the multileaf collimator deviates from the shape specified by a treatment plan, the dose given to a diseased site, which is an irradiation subject, and the distribution of doses differ from the treatment plan; therefore, it is required to rapidly stop the beam irradiation. Accordingly, monitoring, (confirmation) of the leaf positions, which specify the opening shape, and monitoring of the patient position are important functions for realizing the dose set by the treatment plan and need to be of high redundancy and of high multiplicity; thus, a plurality of detection methods are utilized at the same time.

The leaf position detection methods can roughly be divided into a built-in type detection mechanism integrated in each of the leaves or a driving unit corresponding to each leaf and an external (optical) detection method. As the built-in type detection mechanism, for example, there exists a method in which an encoder is provided in a driving motor for driving the leaf and from the number of revolution of the motor, the leaf position is detected. However, in the case of the built-in type detection mechanism, a detecting member needs to be mounted on each leaf or the driving unit corresponding, to each leaf; thus, the complexity of the system is raised. Accordingly, in the case where a plurality of detection methods is redundantly utilized, as one of them, there is adopted, in many cases, an optical (image) type detection method. For example, there has been proposed a particle beam therapy system (for example, refer to Patent Document 1) in which there are provided a built-in type detection mechanism such as an encoder, and there is further provided an optical detection mechanism that takes an image of the opening shape of a leaf by use of a mirror provided in the irradiation field and a camera provided outside the irradiation field and that measures the position of the leaf from the image, so as to monitor the opening shape of the multileaf collimator in a redundant and multiple manner.

Moreover, as another optical detection method, there is proposed a particle beam therapy system (for example, refer to Patent Document 2) in which a screen is provided in the irradiation field and the opening shape projected on the screen is photographed by a camera. Furthermore, there is also proposed a particle beam therapy system (for example, refer to Patent Document 3) in which a collimated laser beam is irradiated onto outer side surface of a leaf and, from the irradiation position, the position of the leaf is detected.

PRIOR ART REFERENCE

Patent Document

[Patent Document 1] Japanese Patent Application Laid-Open No. 2008-295860 (paragraph 0004 and 0021 through 0022, FIGS. 2 and 9)
[Patent Document 2] International Publication No. WO2010/073318A1 (Paragraphs 0015 through 0018, FIG. 1)
[Patent Document 3] Japanese Patent Application Laid-Open No. 2010-104452 (Paragraphs 0037 through 0041, FIGS. 6 through 8)

DISCLOSURE OF THE INVENTION

Problems to be Solved by the Invention

However, in such a particle beam therapy system as disclosed in Patent Document 1 or 2, a foreign material such as a mirror or a screen is included in the irradiation field; therefore, in some cases, because a charged particle beam collides with the mirror or the screen and its energy is reduced, the range of the particle beam is changed or the particle beam is shut off to disperse, whereby irradiation conforming to a treatment plan cannot be performed. Moreover, in the case of such a particle beam therapy system as disclosed in Patent Document 3, it is required to mount a light source and an image-capturing unit outside the movable range of the leaf so that the light source and the image-capturing unit can face the outer side surface of the leaf; therefore, the image capturing device sticks out of the multileaf collimator main body, whereby the system upsizes. In particular, in the case where the light source and the image-capturing unit are provided in the rotating gantry, there has been a problem, for example, that because the moving body increases in volume, it is difficult for the rotating gantry to rotate smoothly and perform multi-port irradiation.

The present invention has been implemented in order to solve the foregoing problems; the objective thereof is to obtain a particle beam therapy system that suppresses dispersion of a charged particle beam, reduction of the energy thereof, and upsizing of the system from being caused by the image capturing unit, and that can accurately monitor the opening shape of the multileaf collimator so as to perform high-accuracy particle beam therapy.

Means for Solving the Problems

A particle beam therapy system according to the present invention is provided with an irradiation nozzle that scans a particle beam supplied from an accelerator and irradiates the particle beam in such a way as to enlarge an irradiation field; a multileaf collimator in which a pair of leaf rows, each of them is composed of a plurality of leaf plates laminated in thickness direction, is arranged in such a way as to interpose a beam axis of the particle beam, in which respective side faces, of the plurality of leaf plates, that face the beam axis are driven in approaching or in departing direction with respect to the beam axis so that a predetermined opening shape is formed, and that forms the particle beam emitted from the irradiation nozzle in such a way that the particle beam conforms to an irradiation subject and then emits the particle beam; and an image-capturing unit that takes images of outer ends, of respective downstream side faces of the plurality of leaf plates in irradiation direction of the particle beam, that are distal with respect to the beam axis, wherein the image-capturing unit is provided for each of the pair of leaf rows, in such a way as to be situated at a position that is at outer side of the irradiation field of the particle beam that has passed through the multileaf collimator and at downstream of the multileaf collimator; and the image-capturing unit is adjusted in such a way that foot of a perpendicular from a viewpoint to the downstream side face, is situated at a position that is at inner side of the position of the outer end when the leaf plate is maximally driven in the departing direction.

Advantage of the Invention

In a particle beam therapy system according to the present invention, the arrangement of devices for taking an image of a multileaf collimator is appropriately adjusted; thus, the irradiation field is not blocked off, and the system is not upsized. As a result, there can be obtained a particle beam therapy system that accurately monitors the opening shape of the multileaf collimator and can perform high-accuracy particle beam therapy.

BEST MODE FOR CARRYING OUT THE INVENTION

Embodiment 1

Figure 1:
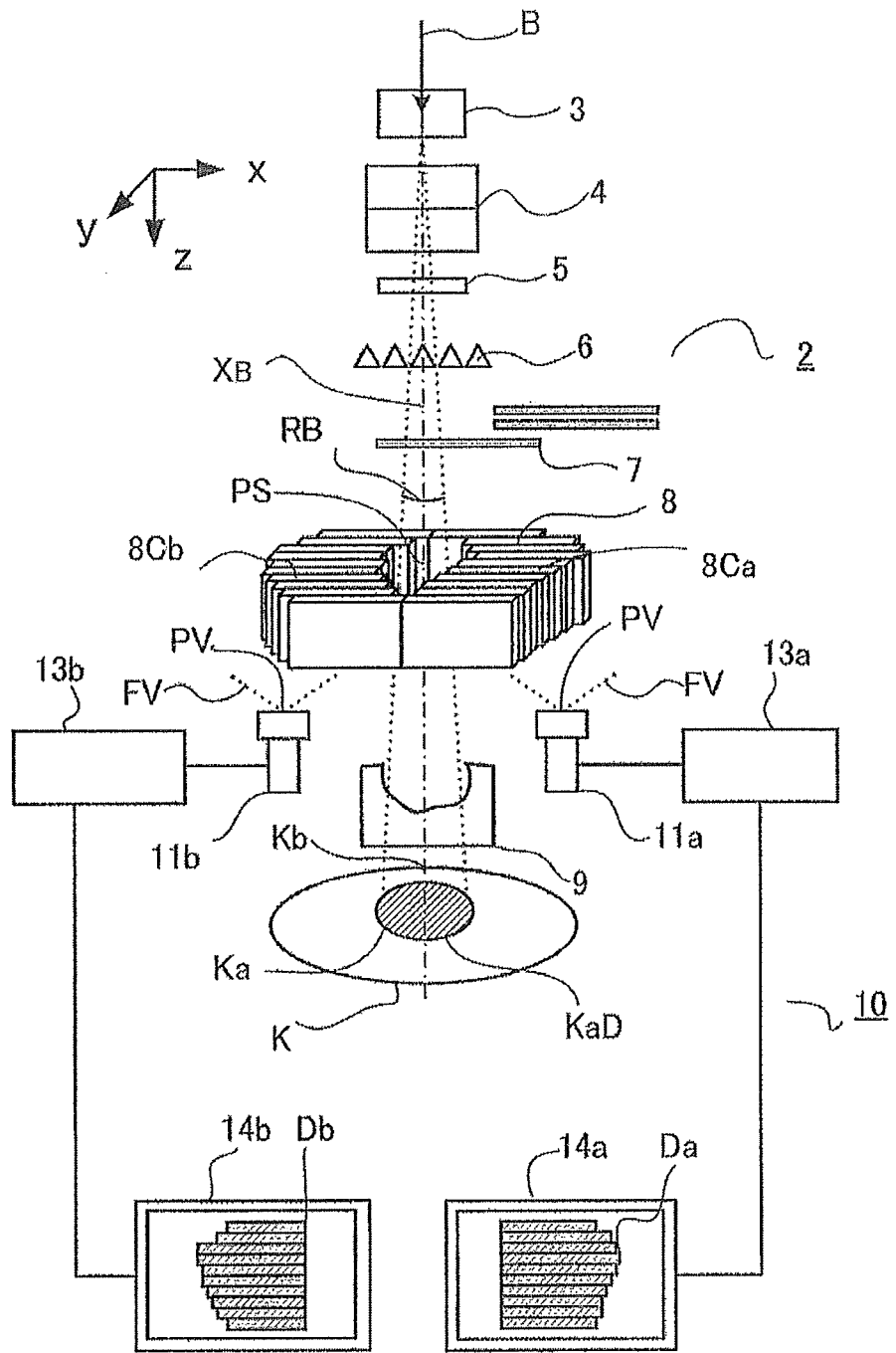
FIG. 1 is a diagram for explaining the configuration of an irradiation system in a particle beam therapy system according to Embodiment 1 of the present invention.
Figure 2:
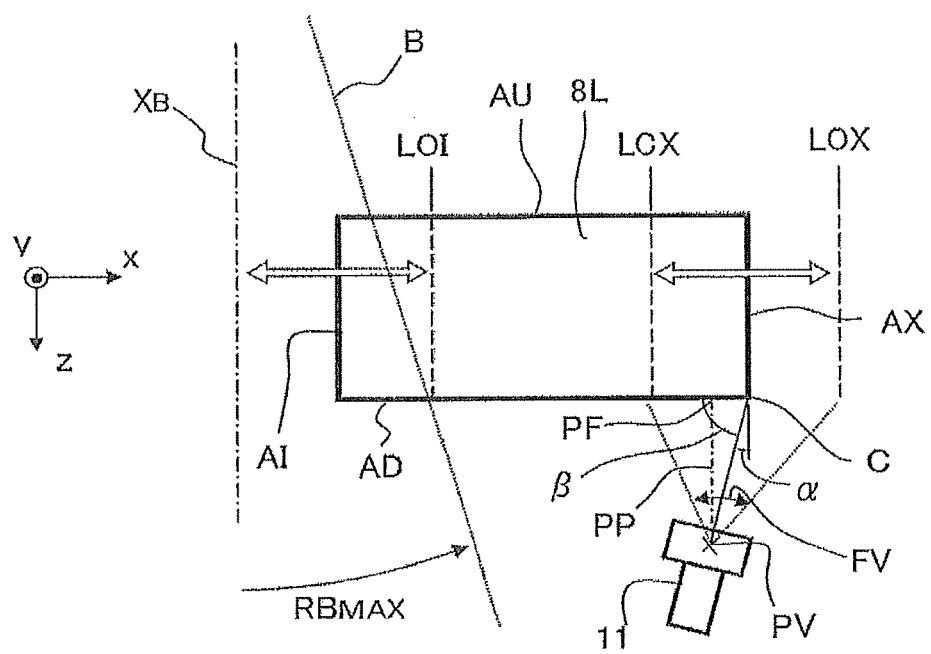
FIG. 2 is a diagram for explaining the positional relationship between a multileaf collimator and an image-capturing unit in a particle beam therapy system according to Embodiment 1 of the present invention.
Figure 3:
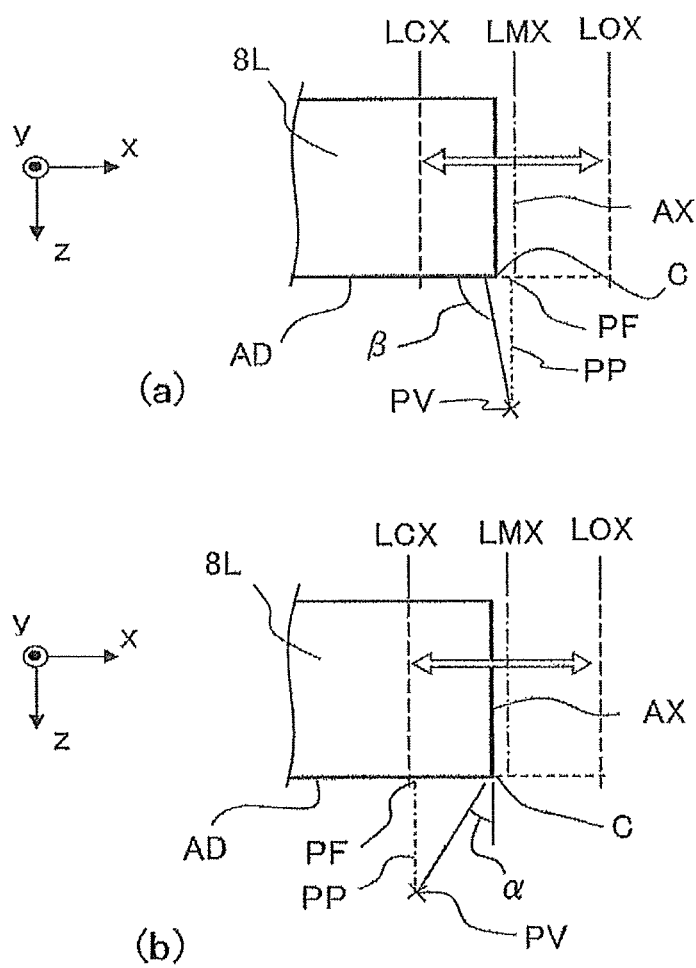
FIG. 3 is a set of diagrams illustrating examples of adjustment of the viewpoint of an image capturing unit that takes an image of a multileaf collimator in a particle beam therapy system according to Embodiment 1 of the present invention.
Figure 4:
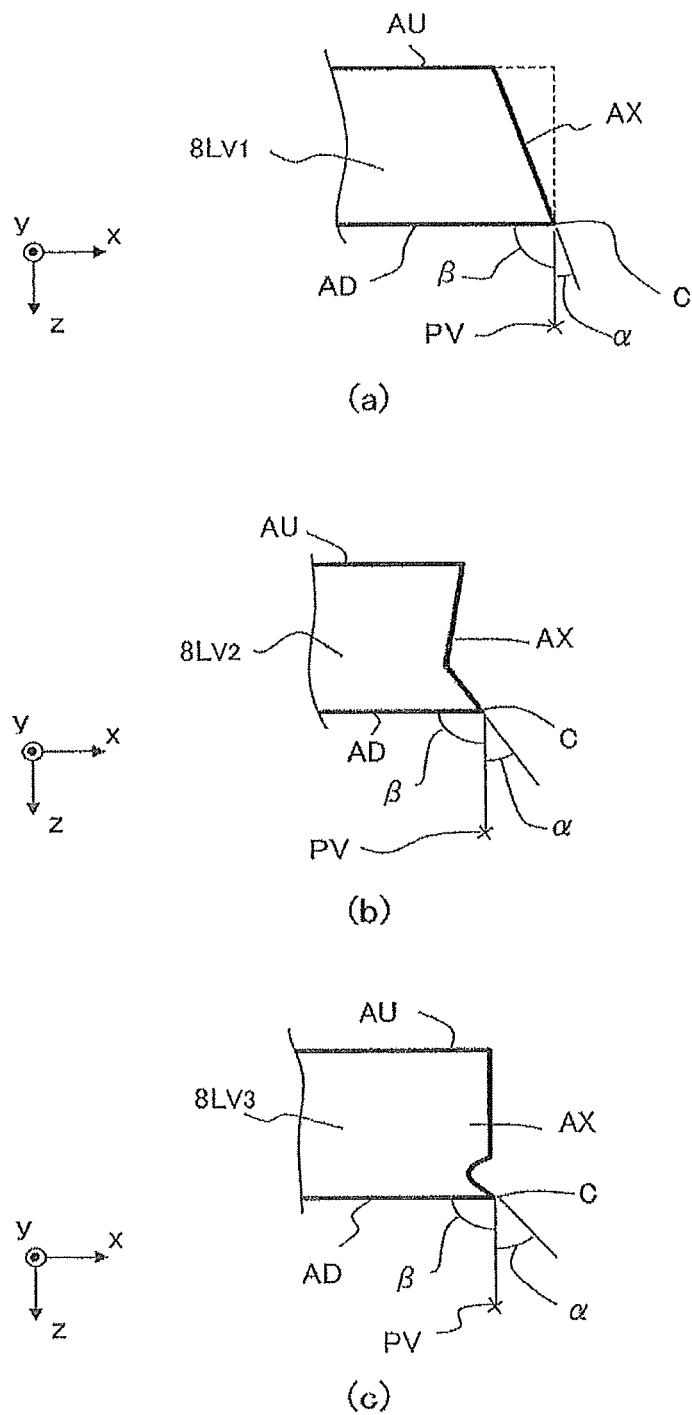
FIG. 4 is a set of diagrams for explaining the positional relationship between a multileaf collimator and an image-capturing unit in a variant example of particle beam therapy system according to Embodiment 1 of the present invention.

FIGS. 1 and 2 are diagrams for explaining the configuration of a particle beam therapy system according to Embodiment 1 of the present invention; FIG. 1 is a diagram illustrating the configuration of the whole irradiation system in a particle beam therapy system; FIG. 2 is a diagram illustrating the positional relationship between a multileaf collimator provided in a particle beam therapy system and an image-capturing unit for taking an image of the multileaf collimator. FIG. 3 is a set of diagrams illustrating examples of adjustment of the viewpoint of an image capturing unit (camera) for accurately detecting the position of a leaf, in a particle beam therapy system according to Embodiment 1 of the present invention. FIG. 4 is a set of diagrams for explaining the positional relationship between the leaf plate of a multileaf collimator and the viewpoint of an image-capturing unit in a variant example of particle beam therapy system according to Embodiment 1 of the present invention.

The largest characteristics of a particle beam therapy system according to Embodiment 1 of the present invention are the installation and the configuration of a shape monitoring device (the image-capturing unit thereof) for detecting the opening shape (positions of respective leaves) of a multileaf collimator. However, before the detailed explanation for the characteristics, there will be explained the overall configuration of the irradiation system in a particle beam therapy system provided with a multileaf collimator. As illustrated in FIG. 1, a particle beam therapy system 2 is provided with a dose monitor 3 that measures the dose of a charged particle beam B supplied from an unillustrated accelerator, a set of wobbler electromagnets 4 that functions as an irradiation nozzle for enlarging an irradiation field RB by circularly scanning the supplied charged particle beam B, a scatterer 5 that is formed of lead or the like and scatters the charged particle beam B, a ridge filter 6 that is formed of aluminum or the like and enlarges the width of a Bragg peak in accordance with the thickness of the irradiation subject, a range shifter 7 that is formed of an acrylic resin or the like and changes the energy (range) of the charged particle beam B in accordance with the depth (irradiation depth) from the body surface of an irradiation subject Ka, a multileaf collimator 8 that is configured with a leaf unit formed of a plurality of leaf plates and a leaf drive mechanism for driving each of leaf plates and that limits an irradiation field in such a way that the irradiation field coincides with the shape of a diseased site, and a bolus 9 that limits the range of the charged particle beam B in such a way that the range coincides with the depth-direction shape of an irradiation subject.

The particle beam therapy system 2 is further provided with video cameras 11a and 11b (collectively referred to as a video camera 11) that are arranged at both respective outer sides that are situated opposite to the opening portion of the multileaf collimator 8 and serve as a shape monitoring device for monitoring an opening shape PS of the multileaf collimator 8, and image processing units 13a and 13b (collectively referred to as an image processing unit 13) that perform processing on respective images taken by the video cameras 11a and 11b; the processed images are displayed, as shape images Da and Db (collectively referred to as a shape image D), by display devices 14a and 14b (collectively referred to as a display device 14), respectively. In FIG. 1, a patient K who undergoes a particle beam therapy is illustrated as a cross section thereof; in the cross section, there are illustrated a diseased site Ka, as an irradiation subject, and a patient position marker Kb for tracking the position of the diseased site Ka being treated.

Next, the operation of enlarging and shaping the irradiation field RB in the irradiation system will be explained.

The charged particle beam B, accelerated by an unillustrated accelerator and supplied by way of a transport system, enters the dose monitor 3, and then the irradiation dose thereof is counted. At this moment, the charged particle beam B that has entered the irradiation system is a so-called pencil beam having a diameter the same as or smaller than several millimeters; the charged particle beam B is scanned by the wobbler electromagnet 4 in such a way as to draw a circular orbit and is scattered by the scatterer 5, so that the irradiation field RB is enlarged. The wobbler electromagnet 4 is usually provided with an x-direction electromagnet and a y-direction electromagnet; the two electromagnets are arranged in such a way as to lie in series along the center axis $X_B$ of the charged particle beam B. Here, for clarity of description, the x direction and the y direction will be defined. The direction ($X_B$ direction) in which the charged particle beam B travels is defined as the positive direction of the z axis. The x axis and the y axis are axes that are perpendicular to the z axis; the x axis and the y axis are also perpendicular to each other. In FIGS. 1, 2, and thereafter, the x direction is defined as the driving direction of a leaf 8L of the multileaf collimator 8; the y direction is defined as the thickness (laminate) direction of the leaf plate 8L. Then, the irradiation field RB is expanded in the xy direction (in the plane direction) by the wobbler electromagnet 4 and the scatterer 5.

Figure 5:
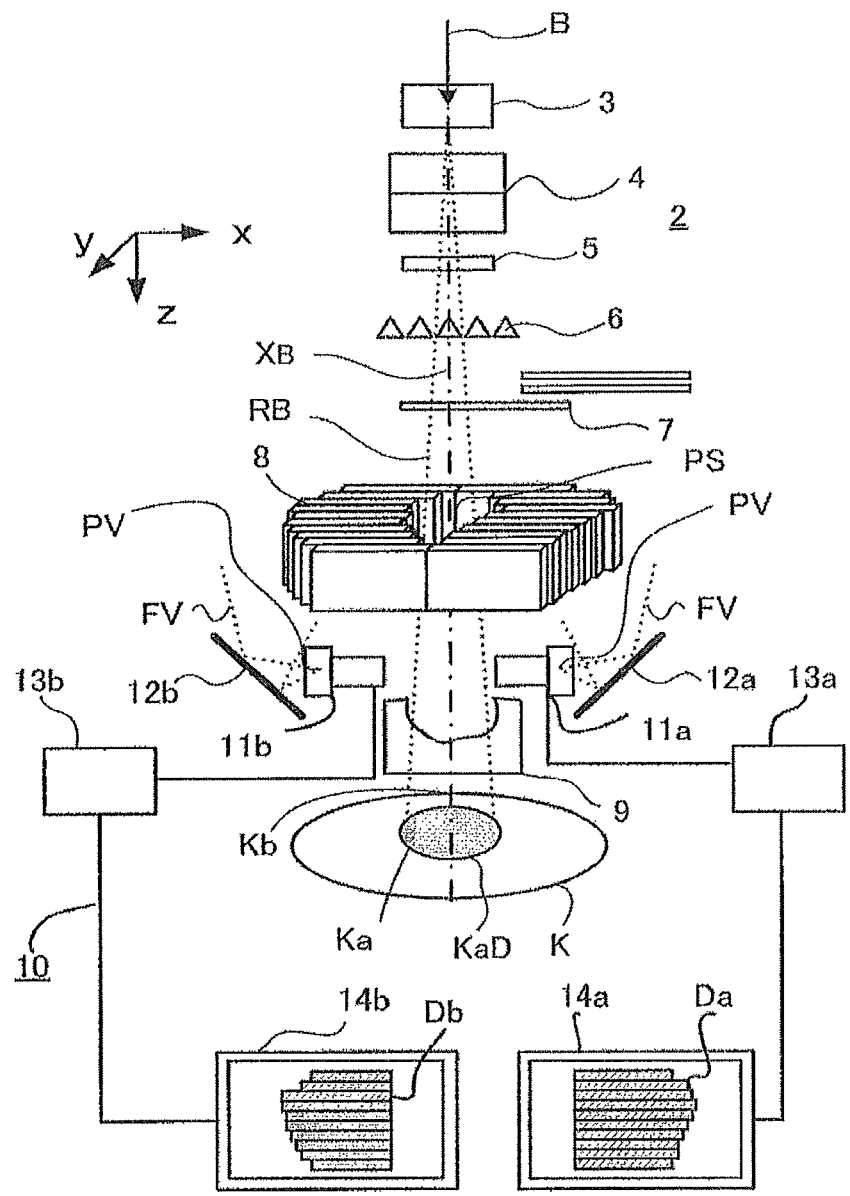
FIG. 5 is a diagram for explaining the configuration of an irradiation system in a particle beam therapy system according to Embodiment 2 of the present invention.

The charged particle beam B whose irradiation field RB has been enlarged passes through the ridge filter 6. The ridge filter is formed, for example, in such a way that a great number of cones or plates whose cross sections are triangles are arranged on a plane; assuming that, for example, the irradiation field RB is divided into a great number of sub-areas, there exist beams B that pass through different thicknesses from one another. For easier understanding, FIG. 1 or 5 illustrates triangular prisms that are arranged in such as way as to be in a row. The Bragg peak is enlarged in such a manner as described above, so that the irradiation field has a predetermined width of SOBP (Spread-Out Bragg Peak). That is to say, the ridge filter 6 enlarges the irradiation field also in the z direction. Next, the charged particle beam B whose irradiation field has been enlarged passes through the range shifter 7. The range shifter 7 is a device that changes the energy of the charged particle beam B. Adjusting the range of the charged particle beam B by the range shifter 7, irradiation of the charged particle beam B (dose delivery) can be performed onto a position of a desired inner-body depth. As described above, the irradiation field is enlarged not only in the plane direction (x, y) but also in the thickness direction (z); however, in this DESCRIPTION, only the enlargement in the plane direction (x, y) is illustrated as the irradiation field RB. As an example of the orbit created by wobbler electromagnet, a circular orbit has been described; however, the orbit is not limited to the foregoing circular orbit but may a spiral orbit or another orbit, as long as it enlarges the irradiation field RB.

Next, the charged particle beam B passes through the multileaf collimator 8. The multileaf collimator 8 is configured with two leaf rows 8C, obtained by laminating tabular leaf plates 8L in the thickness direction (y direction), that are arranged so as to interpose the beam axis $X_B$ and to face each other (in FIG. 1, the right row is indicated by 8Ca, and the left row is indicated by 8Cb). Each of the leaf plates 8L is positioned at a predetermined position along a direction that approaches to or departs from the beam axis $X_B$ within the direction (x) perpendicular to the thickness direction, so that the desired opening shape PS is formed. After that, the irradiation field RB of the charged particle beam B that has passed through the multileaf collimator 8 is limited in accordance with the shape of the diseased site Ka, by means of the opening shape PS conforming to the shape of the diseased site Ka. That is to say, the multileaf collimator 8 performs limitation and formation of the irradiation field RB in the xy direction. The multileaf collimator 8 is provided with at least a cluster of leaf plates 8L and an unillustrated leaf drive mechanism. However, if the leaf drive mechanism itself is drawn in a figure, it becomes difficult to illustrate the arrangement of the leaf plates 8L and the like; therefore, in FIGS. 1, 2, and thereafter, for the sake of simplicity, a cluster of leaf plates 8L is illustrated or a discrete leaf plate 8L is extracted and illustrated.

Lastly, the charged particle beam B passes through the bolus 9. The bolus 9 is a limiter that is formed of resin or the like; it is formed in such a shape as to compensate the depth-direction shape of the diseased site, for example, the distal shape of the diseased site. The distal shape denotes the depression-protrusion contour of the deepest portion KaD. In this situation, the energy of the irradiation field is limited (formed in the z direction) to have a shape the same as the distal shape. That is to say, the bolus 9 performs limitation and formation of the irradiation field in the z direction.

In the case where irradiation utilizing the foregoing irradiation system is performed according to the multi-layer conformal irradiation method, special dose delivery is divided in the depth (z) direction and the dose is given. When irradiation is started, the wobbler electromagnet 4, the range shifter 7, and the multileaf collimator 8 (the opening shape of the multileaf collimator) are set in accordance with the dose delivery for the layers (slices) including the deepest portion KaD, and the charged particle beam B is irradiated onto the diseased site Ka. After the irradiation onto the deepest layer (slice) is completed, the range is automatically adjusted by the range shifter 7 so as to be situated at a position that is shallower (closer to the irradiation source) by a depth corresponding to the Bragg peak width, and the setting of the wobbler electromagnet 4 and the multileaf collimator 8 are also changed; then, irradiation onto the next layer is performed. After that, similarly, the range is adjusted by the range shifter 7, and while the setting of the wobbler electromagnet 4 and the multileaf collimator 8 are changed, the dose optimized for the shape of the diseased site Ka is delivered as a whole.

In order to perform a particle beam therapy in which the level of coincidence (conformity) between the therapy volume and the shape of the diseased site Ka is high, i.e., a high-accuracy particle beam therapy, through such multi-layer conformal irradiation as described above, it is required to confirm and monitor whether or not the opening shape PS of the multileaf collimator 8 is the same as the preliminarily set shape for each irradiation layer (slice). Thus, in the particle beam therapy system 2 according to Embodiment 1, in order to securely monitor the opening shape PS of the multileaf collimator 8, the video camera 11 is disposed as illustrated in FIG. 2.

FIG. 2 illustrates the position of the video camera 11 (the case itself and the viewpoint PV) and the irradiation coverage (irradiation field RB), of the charged particle beam B, that is specified by the driving range of the leaf plate 8L and the leaf plate 8L in the right side of the beam axis $X_B$, when the multileaf collimator 8 is viewed in the y direction. The leaf plate 8L basically has four side faces, i.e., an inner side face AI that is approximately parallel to the traveling direction of the charged particle beam B and faces the beam axis $X_B$, an upstream side face AU that is approximately perpendicular to the traveling direction of the charged particle beam B and is situated at the upstream side (incident side) of the traveling direction of the charged particle beam B, an outer side face AX that is approximately parallel to the traveling direction of the charged particle beam B and is situated at the distal side of the beam axis $X_B$, and a downstream side face AD that is approximately perpendicular to the traveling direction of the charged particle beam B and is situated at the downstream side (emitting side) of the traveling direction of the charged particle beam B. In Embodiment 1, the leaf plate 8L has a rectangular tabular shape, as illustrated in FIG. 2; each leaf plate 8L is driven in such a way that the position thereof can freely be set in the direction (x) that is perpendicular to the beam axis $X_B$ (z) and the lamination (thickness) direction (y) of the leaf plate 8L and is parallel to the side faces AU and AD. The inner side face AI is driven up to LOI when it departs most from the beam axis $X_B$; at this moment, the irradiation coverage of the charged particle beam B becomes maximum ($RB_{MAX}$). The case of the video camera 11 is provided at a position that is outside the maximum irradiation coverage RBMAX and through which the charged particle beam B does not pass, whatever opening shape PS is formed.

Furthermore, the visual field FV of the video camera 11 has the range covering the driving range of the outer side face AX of the leaf plate 8L, i.e., the range from the most approaching position LCX to the most departing position LOX; the video camera 11 is disposed in such a way that when the outer side face AX (strictly speaking, the outer end C (the corner between AD and AX) of the downstream side face AD) is situated at least at outer side of the most approaching position LCX, the line connecting the viewpoint PV with the outer end C is slanted by "α" from the outer side face X. In addition, the video camera 11 is disposed in such a way that at a certain point within the driving range of the outer end C, the angle between the line connecting the viewpoint PV with the outer end C and the downstream side face AD becomes a right angle. The left-hand camera 11b is disposed in the same manner as the camera 11a.

The video camera 11 provided as described above takes an image in such a way as to include the outer end C, within the downstream side face AD of the leaf plate 8L, that is situated at the opposite side of the inner side face AI that forms the opening shape PS. As illustrated in FIG. 1, the image taken by the right-hand video camera 11a is processed by the right-hand image processing unit 13a and becomes a right-hand collimator shape image Da. Also in the left-hand side of the beam axis XB, the image taken by the left-hand video camera 11b is processed by the left-hand image processing unit 13b and becomes a left-hand collimator shape image Db. In this situation, when the distance between the inner side face AI and the outer side face AX (outer end C) is offset, there is obtained the position of the inner side face AI; when the space (the portion of the downstream side face AD) and the shielding material (the other portion) are reversed on the outer end C as the boundary, there is obtained the opening shape PS (the position of the inner side face AI of each leaf plate 8L) of the multileaf collimator 8.

As described above, the video camera 11 takes an image of the outer end C, within the downstream side face AD of the leaf plate 8L, that is situated at the opposite side of the opening portion; therefore, it is made possible that without interrupting the irradiation field RB of the charged particle beam B, the visual field FV of the video camera 11 can perpendicularly face (β becomes a right angle) the downstream side face AD of the multileaf collimator 8. Accordingly, in the case where, for example, as illustrated in FIG. 3(a), while it is prioritized that β becomes a right angle (90), adjustment is performed in such a way that the foot PF of a perpendicular line PP from the viewpoint PV to the downstream side face AD is located in the vicinity (in the range closer to the middle LMX than to LCX or LOX) of a position LMX of the outer side face AX (strictly speaking, the outer end C of the downstream side face AD) when the leaf plate 8L is moved to the middle of the driving range thereof, the angle β swings within an angle that is the same as or smaller than the half of the visual field FV, with respect to 90°; thus, regardless of the driving position of the leaf plate 8L, a uniform contrast can be obtained, whereby the visibility is enhanced. In addition, in the case where the outer end C is located at a position with which the angle β largely deviate from a right angle, the image processing unit 13 corrects distortion in an image, so that there can be created a multileaf collimator shape image D that is equivalent to that at a time when the opening shape PS is directly viewed along the beam axis $X_B$.

In the case where, for example, as illustrated in FIG. 3(b), while it is prioritized that a range in which the slant α between a line from the viewpoint PV to the outer end C and the outer side face AX is positive is made wide, adjustment is performed in such a way that the foot PF of the perpendicular line PP from the viewpoint PV to the downstream side face AD is located in the vicinity (in the range closer to LCX than to the middle LMX) of the position LOX of the outer end C when the leaf plate 8L is moved to the most approaching position, a taken image does not include the outer side face AX or even when the taken image includes the outer side face AX, the angle is small; thus, the distinction between the downstream side face AD and the outer side face AX can readily be performed, whereby the position of the outer end (edge) C can accurately be detected. In the case where the viewpoint PV is situated at a position of inner side (the beam axis $X_B$ side) of LCX, there exists no portion that perpendicularly faces the downstream side face AD; however, no taken image includes the outer side face AX. In each of FIGS. 3(a) and 3(b), there are extracted and illustrated only the viewpoint PV of the video camera 11 and the portion, of the leaf plate 8L, that is in the vicinity of the outer side face AX.

In FIG. 1, there is illustrated an example in which the display devices 14a and 14b for the right and left shape images Da and Db are separately arranged; however, the present invention is not limited thereto. For example, it may be allowed that image data pieces of the video cameras 11a and 11b are collectively image-processed, converted into the form of the opening shape PS, and displayed by a single display device. Moreover, it may also be allowed that not only the shape image D is simply displayed, but also, for example, a preliminarily stored pattern and the shape image are compared with each other so that the image data is converted into numerical data such as a driving distance or a driving angle that indicates the position of the leaf. In this situation, for example, there may be provided a determination device that performs comparison between data of such a built-in position detection device as explained in "Background Art" herein and data obtained from an image and then determines whether or not there exists an abnormality in the position of the leaf, the position detection device, or the driving mechanism, based on the level of coincidence between the data pieces (for example, based on whether the difference is smaller or not smaller than a threshold value).

Variant Example of Embodiment 1

With regard to the relationship between the viewpoint PV and the leaf plate 8L, illustrated in FIG. 3, even in the case where, in addition to Embodiment 1, it is assumed that the orbit is a circumference orbit and the multileaf collimator has a shape such as the outer portion of a sector obtained by simply dividing a ring in the radial direction, there is assumed a basic form in which neighboring side faces (or the tangential lines thereof) cross each other at an angle of 90° and there exists a restriction of α+β=90. Accordingly, in the case where a position where β becomes a right angle is prioritized and, as illustrated in FIG. 3(a), there is performed setting in which the foot PF of the perpendicular line PP drawn from the viewpoint PV is situated in the vicinity of the middle LMX in the driving range of the outer end C, the range where α is positive becomes as narrow as less than the half of the driving range. However, in the case where, as leaf plates $8L_{v1}$ through $8L_{v3}$ (collectively referred to as $8L_v$) in a variant example illustrated in FIGS. 4(a) through 4(c), the angle of the outer side face AX is changed from a basic form to an acute angle from the downstream side face, the range where a is kept to be a positive value can be expanded, even when the position at which β becomes a right angle is set to be in the vicinity of the middle LMX of the driving range of the outer side face AX (strictly speaking, the outer end C of the downstream side face AD) of the leaf plate $8L_v$. As is the case in FIG. 3, in each of FIGS. 4(a) through 4(c), there are extracted and illustrated only the viewpoint PV of the video camera 11 and the portion, of the leaf plate $8L_v$, that is in the vicinity of the outer side face AX.

In this situation, in the case where, for example, as the leaf plate $8L_{v1}$ illustrated in FIG. 4(a), the overall outer side face AX has a constant gradient with respect to the downstream side face AD, α is positive in the whole driving range of the leaf plate. Therefore, because the video camera 11 does not take any image of the outer side face AX, the outer end C can securely be recognized. The dotted line indicates the side faces of the rectangular leaf plate 8L. Alternatively, in the case where as the leaf plate $8L_{v2}$ illustrated in FIG. 4(b), only the portion (the portion close to the downstream side face AD), of the outer side face AX, that is in the vicinity of the outer end C is made to have an acute angle, the video camera 11 does not take an image of the portion. In this case, the video camera 11 may take an image of the portion, of the outer side face AX, that is apart from the outer end C; however, because compared to the side face AD, the portion is away from the viewpoint PV, the outer end C can readily be recognized. Moreover, in the case where as the leaf plate $8L_{v3}$ illustrated in FIG. 4(c), the portion (the portion close to the downstream side face AD), of the outer side face AX, that is in the vicinity of the outer end C is curved surface, the tangential line of the portion that makes contact with the outer end C may have an acute angle with respect to the downstream side face AD.

As described above, the video camera 11 for monitoring the opening shape PS is disposed at a position that is at outer side of the irradiation field RB; thus, there occurs no case where the charged particle beam B collides with the image-capturing unit and hence the dispersion or the energy reduction is caused. Furthermore, the foot PF of the perpendicular line PP from the viewpoint PV of the video camera 11 to the downstream side face AD is situated at a position that is at inner side (the irradiation field RB side) of the position LOX of the outer end C of the downstream side face AD when the leaf plate 8L is driven to the most departing position; therefore, the image capturing device is suppressed from projecting from the main body of the multileaf collimator 8, whereby the irradiation system can be made compact. Accordingly, even when the image capturing device is disposed in the rotating gantry, the size of the moving body is suppressed, whereby rotating movement can readily be performed.

As a result, it is made possible that even when irradiation is being implemented, the opening shape PS of the multileaf collimator 8 is confirmed and monitored, without interrupting irradiation of a charged particle beam; for example, by redundantly performing monitoring along with a built-in position detection device, the possibility of erroneous irradiation is reduced, whereby there can be configured a particle beam therapy system that can perform high-accuracy particle beam therapy the above example, as the image-capturing unit, a video camera is utilized; however, the monitoring can also be performed by a still camera.

The perpendicular line PP and the foot PF thereof, the angles α and β, and the like in the foregoing explanation or the explanation, described later denote positions and angles when viewed from the thickness direction (y) of the leaf plate 8L, i.e., positions and angles in the xz plane; positions and angles in the lamination direction (y) in the leaf row 8C are not specified.

As described above, the particle beam therapy system 2 according to Embodiment 1 is provided with the wobbler electromagnet 4 and the scatterer 5 that function as an irradiation nozzle for scanning the charged particle beam B supplied from an accelerator and irradiating the charged particle beam B in such a way as to enlarge the irradiation field RB; a multileaf collimator 8 in which a pair of leaf rows 8C, each of them is composed of a plurality of leaf plates 8L laminated in the thickness, is arranged in such a way as to interpose a beam axis $X_B$ of the charged particle beam B, in which respective side faces AI, of the plurality of leaf plates 8L, that face the beam axis $X_B$ are driven in approaching or in departing direction with respect to the beam axis $X_B$ so that the predetermined opening shape PS is formed, and that forms the particle beam B emitted from an irradiation nozzle in such a way that it conforms to an irradiation subject and then emits it; and video camera 11 that is an image-capturing unit that takes an image of each of the outer ends C, of respective downstream side faces AD of the plurality of leaf plates 8L in irradiation direction of the particle beam B, that are distal with respect to the beam axis $X_B$, in order to monitor the opening shape PS. The image-capturing unit 11 is provided for each of the pair of leaf rows 8C, in such a way as to be situated at a position that is at outer side of the irradiation field RB of the particle beam B that has passed through the multileaf collimator 8, and at downstream of the multileaf collimator 8; furthermore, the image-capturing unit 11 is adjusted in such a way that foot PF of a perpendicular PP from a viewpoint PV to the downstream side face AD, is situated at a position that is at inner side of the position LOX of the outer end C when the leaf plate 8L is maximally driven in the departing direction. As a result, dispersion of a charged particle beam, reduction of the energy thereof, and upsizing of the system is suppressed from being caused and the outer end C of the leaf plate 8L is securely recognized, so that the opening shape PS of the multileaf collimator 8 can accurately be monitored. Thus, it is made possible that even when irradiation is being implemented, the opening shape PS of the multileaf collimator is confirmed and monitored, without interrupting irradiation of the charged particle beam B; for example, by redundantly performing monitoring along with a built-in position detection device, the possibility of erroneous irradiation is reduced, whereby there can be configured a particle beam therapy system that can perform high-accuracy particle beam therapy.

Moreover, the shape monitoring device 10 is configured in such a way as to include the image processing unit 13 that determines the position of the outer end C, based on an image taken by the image-capturing unit 11, and performs conversion processing in which the position of the outer end C is converted into data that indicates the opening shape PS; therefore, the opening shape PS of the multileaf collimator 8 can quantitatively be evaluated, and by making comparison with data from another monitoring device, the opening shape can further securely be monitored.

In this situation, in the case where foot PF of a perpendicular PP from the viewpoint PV to the downstream side face AD is located at a position that is closer to a position LMX of the outer end C at a time when the leaf plate 8L is moved to a middle of driving range than to a position LOX of the outer end C at a time when the leaf plate 8L is maximally moved in the approaching direction, the angle β swings within an angle that is the same as or smaller than the half of the visual field FV, with respect to 90°; thus, there is expanded the range where the image of the outer end C is approximately perpendicularly taken, and hence regardless of the driving position of the leaf plate 8L, a uniform contrast can be obtained, whereby the visibility is enhanced.

Furthermore, in the case where at least the portion, of an outer side face AX, that is adjacent to the downstream side face AD, has an acute angle with respect to the downstream side face AD, α can be positive in the whole driving range of the leaf plate, even when the foot PF of perpendicular PP is situated in the vicinity of the middle LMX and the angle β is prioritized. Therefore, because the video camera 11 does not take any image of the outer side face AX, the outer end C can further securely be recognized based on an image including less distortion and having a high contrast.

Alternatively, in the case where foot PF of perpendicular PP from the viewpoint PV to the downstream side face AD is located at a position that is closer to a position LCX of the outer end C at a time when the leaf plate 8L is maximally moved in the approaching direction than to a position of the outer end C at a time when the leaf plate 8L is moved to a middle of driving range, there is expanded the range where the gradient α of the line from the viewpoint PV to the outer end C with respect to the outer side face AX, becomes positive; thus, the taken image does not include the outer side face AX, or even when the outer side face AX is included, the angle becomes small. As a result, the distinction between the downstream side face AD and the outer side face AX can readily be performed, whereby the position of the outer end C can accurately be detected.

Embodiment 2

In Embodiment 1, there has been described a case where an image is obtained by directly viewing the edge portion C of the downstream side face AD of the leaf plate through the video camera 11; however, in Embodiment 2, there is further provided a mirror; through the mirror, there is taken an image of the edge portion C of the downstream side face AD of the leaf plate 8L.

Figure 6:
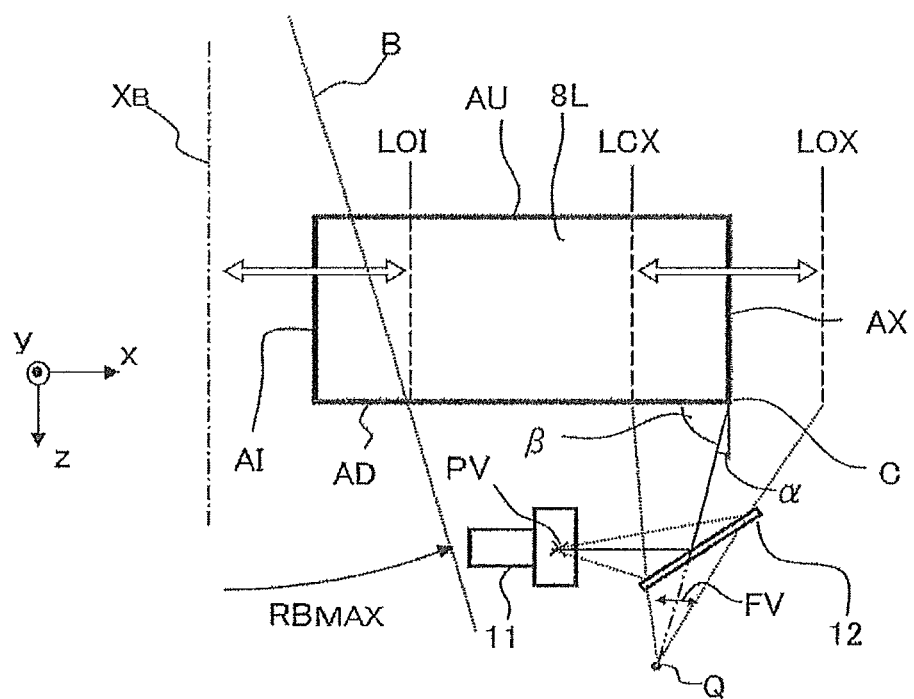
FIG. 6 is a diagram for explaining the positional relationship between a multileaf collimator and an image-capturing unit in a particle beam therapy system according to Embodiment 2 of the present invention.
Figure 7:
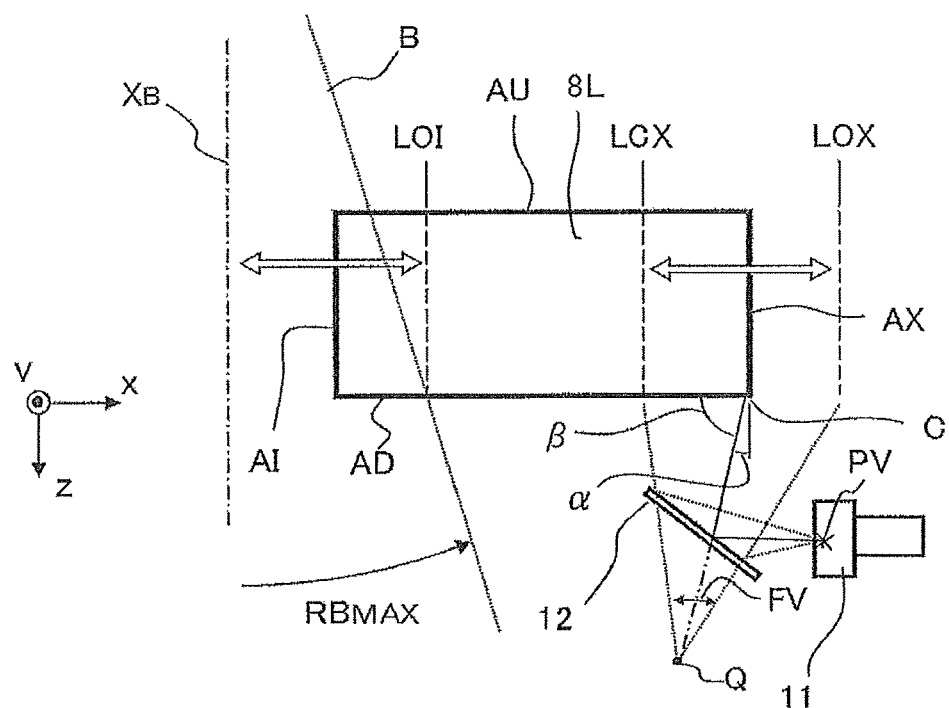
FIG. 7 is a set of diagrams for explaining the positional relationship between a multileaf collimator and an image-capturing unit in a variant example of particle beam therapy system according to Embodiment 2 of the present invention.

FIGS. 5 and 6 are diagrams for explaining the configuration of a particle beam therapy system according to Embodiment 2 of the present invention; FIG. 5 is a diagram illustrating the configuration of the whole irradiation system in a particle beam therapy system; FIG. 6 is a diagram illustrating the positional relationship between a multileaf collimator provided in a particle beam therapy system and a shape monitoring device of the multileaf collimator. FIG. 7 is a set of diagrams for explaining the positional relationship between a leaf plate of a multileaf collimator and a shape monitoring device in a variant example of particle beam therapy system according to Embodiment 2 of the present invention.

As illustrated in FIG. 5, the right visual field shape monitoring mirror 12a and the left visual field shape monitoring mirror 12b (collectively, referred to as a mirror 12) are arranged at respective positions that are at the downstream side of the multileaf collimator 8 in the irradiation direction of the charged particle beam B and are right-outer side and left-outer side with respect to the irradiation field RB; the image of the outer end C (edge portion) of the downstream side face AD of each leaf plate 8L is reflected by the right visual field shape monitoring mirror 12a and the left visual field shape monitoring mirror 12b, and the right visual field video camera 11a and the left visual field video camera 11b each take a picture of that image from the downstream side of the multileaf collimator. In this situation, in the case where as illustrated in FIG. 6, instead of the viewpoint PV, the virtual image Q, of the viewpoint PV, that is formed by the mirror 12 is disposed at the position described in Embodiment 1, the same effect as that in Embodiment 1 can be demonstrated. Moreover, the flexibility of arranging the image-capturing unit is raised and the distance between the viewpoint PV and the end C, which is an imaging subject, can be made long; thus, the angle of the visual field FV can be reduced and hence the angle for performing image-capturing in a wide region out of the driving range becomes small, whereby the accuracy of determining the position is raised.

Variant Example of Embodiment 2

In each of FIGS. 5 and 6, there has been illustrated an example where the video camera 11 is disposed at a position that is inner side of the mirror 12; however, the present invention is not limited thereto. For example, as illustrated in FIG. 7, the video camera 11 may be disposed at a position that is outer side of the mirror 12. When the video camera 11 is disposed at a position that is outer side of the mirror 12, the positional adjustment of the visual point (the virtual image Q thereof) can readily be performed with the image-capturing unit (the camera 11 and the mirror 12) unincluded in the irradiation field RB, even in the case where the distance between the irradiation field RB and the position LOX of the outer end C at a time when the leaf plate 8L approach each other most closely is small. Still moreover, it is not necessarily required that only a single mirror 12 is utilized; it may be allowed that a plurality of mirrors fold back the optical path.

As described above, in the particle beam therapy system according to Embodiment 2, the image-capturing unit includes a mirror 12 that reflects the image of the outer end C of the downstream side face AD of the leaf plate 8L and a video camera 11 that is an image-capturing device disposed at a position that is away from the mirror 12, and the arrangement of the mirror 12 and the image-capturing device 11 is adjusted, based on a virtual image Q, of the viewpoint PV of the image-capturing device 11, that is caused by the reflection of the mirror 12; therefore, the flexibility of arranging the image-capturing unit is raised and the distance between the viewpoint PV and the outer end C, which is an imaging subject, can be made long; thus, the angle of the visual field FV can be reduced and hence the angle for performing image-capturing in a wide region out of the driving range of the leaf plate 8L becomes small, whereby the accuracy of determining the position is raised.

DESCRIPTION OF REFERENCE NUMERALS

2: particle beam therapy system
3: dose meter
4: wobbler electromagnet (irradiation nozzle)
5: scatterer (irradiation nozzle)
6: ridge filter
7: range shifter
8: multileaf collimator
8C: leaf row
8C: leaf plate
9: bolus
10: shape monitoring device
11: camera (image-capturing unit)
12: mirror (image-capturing unit)
13: image processing unit
14: image display device
AI: inner side face of leaf plate
AD: downstream side face of leaf plate
AU: upstream side face of leaf plate
AX: outer side face of leaf plate
B: charged particle beam (particle beam)
C: outer end (edge portion) of downstream side face of leaf plate
D: processing image
FV: visual field of image-capturing unit
LCX: position of outer end at the timing of closest approach LMX: position of outer end at the timing of being at middle of driving range
LOI: position of inner side face at the timing of being apart most
LOX: position of outer end at the timing of being apart most
PF: foot of perpendicular line between viewpoint and downstream side face
PP: perpendicular line between viewpoint and downstream side face
PS: opening shape
PV: viewpoint of image-capturing unit
Q: optical viewpoint (virtual image of viewpoint) of image-capturing unit
RB: irradiation field
α: angle between outer side face and line from viewpoint to outer end of downstream side face
β: angle between downstream side face and line from viewpoint to outer end of downstream side face

The invention claimed is:

1. A particle beam therapy system comprising:
an irradiation nozzle that scans a particle beam supplied from an accelerator and irradiates the particle beam in such a way as to enlarge an irradiation field;
a multileaf collimator in which a pair of leaf rows, each being composed of a plurality of leaf plates laminated in a thickness direction, is arranged in such a way as to interpose a beam axis of the particle beam, in which respective side faces of the plurality of leaf plates, that face the beam axis, are driven in an approaching or in a departing direction with respect to the beam axis so that a predetermined opening shape (i) is formed, and that conforms the particle beam emitted from the irradiation nozzle to an irradiation subject and (ii) emits the particle beam; and
an image-capturing unit that takes images of outer ends, of respective downstream side faces of the plurality of leaf plates in irradiation direction of the particle beam, that are distal with respect to the beam axis, wherein
the image-capturing unit is provided for each of the pair of leaf rows, in such a way as to be situated at a position that is at an outer side of the irradiation field of the particle beam that has passed through the multileaf collimator and downstream of the multileaf collimator, and
the image-capturing unit is adjusted in such a way that a foot of a perpendicular line from a viewpoint, of the image-capturing unit, to the downstream side face of a leaf plate, is situated at a position that is at an inner side of a position of an outer end of the leaf plate when the leaf plate is maximally driven in the departing direction.

2. The particle beam therapy system according to claim 1, wherein the image-capturing unit has a mirror that reflects an image of the outer end of the leaf plate and an image-capturing device provided apart from the mirror,
and arrangement of the mirror and the image-capturing device is adjusted, based on a virtual image of the viewpoint of the image-capturing device, that is caused by reflection of the mirror.

3. The particle beam therapy system according to claim 2, wherein the image-capturing unit is adjusted in such a way that the foot of a perpendicular line from the viewpoint to the downstream side face is located at a position that is closer to a position of the outer end at a time when the leaf plate is moved to a middle of driving range than to a position of the outer end at a time when the leaf plate is maximally moved in the approaching direction.

4. The particle beam therapy system according to claim 3, wherein each of the plurality of leaf plates is formed in such a way that at least a portion, of an outer side face of the leaf plate, that is adjacent to the downstream side face, has an acute angle with respect to the downstream side face.

5. The particle beam therapy system according to claim 4, further including an image processing unit that determines the position of the outer end, based on an image taken by the image-capturing unit, and performs conversion processing in which the position of the outer end is converted into data that indicates the opening shape.

6. The particle beam therapy system according to claim 3, further including an image processing unit that determines the position of the outer end, based on an image taken by the image-capturing unit, and performs conversion processing in which the position of the outer end is converted into data that indicates the opening shape.

7. The particle beam therapy system according to claim 2, wherein the image-capturing unit is adjusted in such a way that the foot of a perpendicular line from the viewpoint to the downstream side face is located at a position that is closer to a position of the outer end at a time when the leaf plate is maximally moved in the approaching direction than to a position of the outer end at a time when the leaf plate is moved to a middle of driving range.

8. The particle beam therapy system according to claim 7, further including an image processing unit that determines the position of the outer end, based on an image taken by the image-capturing unit, and performs conversion processing in which the position of the outer end is converted into data that indicates the opening shape.

9. The particle beam therapy system according to claim 2, further including an image processing unit that determines the position of the outer end, based on an image taken by the image-capturing unit, and performs conversion processing in which the position of the outer end is converted into data that indicates the opening shape.

10. The particle beam therapy system according to claim 1, wherein the image-capturing unit is adjusted in such a way that the foot of a perpendicular in from the viewpoint to the downstream side face is located at a position that is closer to a position of the outer end at a time when the leaf plate is moved to a middle of driving range than to a position of the outer end at a time when the leaf plate is maximally moved in the approaching direction.

11. The particle beam therapy system according to claim 10, wherein each of the plurality of leaf plates is formed in such a way that at least a portion, of an outer side face of the leaf plate, that is adjacent to the downstream side face, has an acute angle with respect to the downstream side face.

12. The particle beam therapy system according to claim 11, further including an image processing unit that determines the position of the outer end, based on an image taken by the image-capturing unit, and performs conversion processing in which the position of the outer end is converted into data that indicates the opening shape.

13. The particle beam therapy system according to claim 10, further including an image processing unit that determines the position of the outer end, based on an image taken by the image-capturing unit, and performs conversion processing in which the position of the outer end is converted into data that indicates the opening shape.

14. The particle beam therapy system according to claim 1, wherein the image-capturing unit is adjusted in such a way that the foot of a perpendicular line from the viewpoint to the downstream side face is located at a position that is closer to a position of the outer end at a time when the leaf plate is maximally moved in the approaching direction than to a position of the outer end at a time when the leaf plate is moved to a middle of driving range.

15. The particle beam therapy system according to claim 14, further including an image processing unit that determines the position of the outer end, based on an image taken by the image-capturing unit, and performs conversion processing in which the position of the outer end is converted into data that indicates the opening shape.

16. The particle beam therapy system according to claim 1, further including an image processing unit that determines the position of the outer end, based on an image taken by the image-capturing unit, and performs conversion processing in which the position of the outer end is converted into data that indicates the opening shape.

* * * * *